US009005604B2

(12) United States Patent
Scott-Carnell et al.

(10) Patent No.: US 9,005,604 B2
(45) Date of Patent: Apr. 14, 2015

(54) ALIGNED AND ELECTROSPUN PIEZOELECTRIC POLYMER FIBER ASSEMBLY AND SCAFFOLD

(75) Inventors: Lisa A. Scott-Carnell, Norfolk, VA (US); Emilie J. Siochi, Newport News, VA (US); Nancy M. Holloway, White Marsh, VA (US); Kam W. Leong, Durham, NC (US); Karina Kulangara, Durham, NC (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 12/969,076

(22) Filed: Dec. 15, 2010

(65) Prior Publication Data
US 2011/0142806 A1 Jun. 16, 2011

Related U.S. Application Data

(60) Provisional application No. 61/286,484, filed on Dec. 15, 2009.

(51) Int. Cl.
C12N 11/08 (2006.01)
C12N 13/00 (2006.01)
A61L 27/16 (2006.01)
A61L 27/38 (2006.01)
C12N 5/00 (2006.01)
A61K 35/12 (2006.01)

(52) U.S. Cl.
CPC ............... *C12N 11/08* (2013.01); *A61L 27/16* (2013.01); *A61L 27/3834* (2013.01); *C12N 5/0068* (2013.01); *C12N 13/00* (2013.01); *A61K 35/12* (2013.01); *C12N 2533/30* (2013.01)

(58) Field of Classification Search
None
See application file for complete search history.

(56) References Cited

U.S. PATENT DOCUMENTS

| 5,219,659 | A | 6/1993 | Weber et al. |
| 5,964,783 | A | 10/1999 | Grafton et al. |
| 6,190,893 | B1 | 2/2001 | Shastri et al. |
| 6,569,654 | B2 * | 5/2003 | Shastri et al. ............... 435/173.8 |
| 6,582,383 | B2 | 6/2003 | Horning |
| 6,809,462 | B2 | 10/2004 | Pelrine et al. |
| 7,112,293 | B2 | 9/2006 | Dubson et al. |
| 2003/0146757 | A1 | 8/2003 | Aguero et al. |
| 2006/0018954 | A1 | 1/2006 | Kuttler |
| 2006/0057377 | A1 | 3/2006 | Harrison et al. |
| 2006/0094112 | A1 | 5/2006 | Babalola et al. |
| 2007/0042069 | A1 | 2/2007 | Armantrout et al. |
| 2007/0282378 | A1 | 12/2007 | Huang et al. |
| 2008/0110342 | A1 | 5/2008 | Ensor et al. |
| 2008/0238256 | A1 * | 10/2008 | Leija et al. ............... 310/328 |
| 2009/0108503 | A1 | 4/2009 | Scott-Carnell et al. |
| 2009/0325293 | A1 | 12/2009 | Davis et al. |
| 2009/0325296 | A1 | 12/2009 | Arinzeh et al. |
| 2010/0201384 | A1 | 8/2010 | Scott-Carnell et al. |
| 2010/0211151 | A1 * | 8/2010 | Scott-Carnell et al. ....... 607/149 |
| 2010/0222771 | A1 | 9/2010 | Mitchell et al. |
| 2011/0142806 | A1 | 6/2011 | Scott-Carnell et al. |

FOREIGN PATENT DOCUMENTS

WO 2006-018838 A2 2/2006
WO WO 2006138718 A2 * 12/2006

OTHER PUBLICATIONS

Lee, Y-S; et al; "An Electroactive Conduit for Spinal Cord Injury Repair." Bioengineering Conference, 2009 IEEE 35th Annual Northeast.*
Moutos, Franklin T; et al; "A biomimetic three-dimensional woven composite scaffold for functional tissue engineering of cartilage." Nature Materials, 6, 162-167, 2007.*
Neuss, Sabine; et al; "Assesment of stem cell/biomaterial combinations for stem cell-based tissue engineering." Biomaterials, 29, 302-313, 2008.*
Allcock, Harry R; et al; Contemporary Polymer Chemistry, Pearson Education, 3rd Edition, 2003, 732-736.*
Xie, Jingwei; et al; "Putting Electrospun Nanofibers to Work for Biomedical Research" Macromolecular Rapid Communications, 29, 1775-1792, 2008.*
Jun, Indong; et al; "The stimulation of myoblast differentiation by electrically conductive sub-micron fibers" Biomaterials, 30, 2038-2047, 2009.*
Yu, Laura Y; et al; "Promoting neuron adhesion and growth" Materials Today, 11, 36-42, 2008.*

(Continued)

*Primary Examiner* — Blaine Lankford
*Assistant Examiner* — David Berke-Schlessel
(74) *Attorney, Agent, or Firm* — Jennifer L. Riley; Andrea Z. Warmbier; Thomas K. McBride

(57) ABSTRACT

A scaffold assembly and related methods of manufacturing and/or using the scaffold for stem cell culture and tissue engineering applications are disclosed which at least partially mimic a native biological environment by providing biochemical, topographical, mechanical and electrical cues by using an electroactive material. The assembly includes at least one layer of substantially aligned, electrospun polymer fiber having an operative connection for individual voltage application. A method of cell tissue engineering and/or stem cell differentiation uses the assembly seeded with a sample of cells suspended in cell culture media, incubates and applies voltage to one or more layers, and thus produces cells and/or a tissue construct. In another aspect, the invention provides a method of manufacturing the assembly including the steps of providing a first pre-electroded substrate surface; electrospinning a first substantially aligned polymer fiber layer onto the first surface; providing a second pre-electroded substrate surface; electrospinning a second substantially aligned polymer fiber layer onto the second surface; and, retaining together the layered surfaces with a clamp and/or an adhesive compound.

19 Claims, 5 Drawing Sheets

(56) References Cited

OTHER PUBLICATIONS

Li, Mengyan; et al; "Electrospinning polyaniline-contained gelatin nanofibers for tissue engineering applications" Biomaterials, 27, 2705-2715, 2006.*

Wu et al, Control of Electrospun Mat Width through the use of Parallel Auxillary Electrodes. Polymer, 2007, vol. 48, pp. 5653-5661.

C. S. Kong et al, Nano-web formation by the electrospinning at various electric fields. J Mater Sci (2007) 42:8106-8112.

Bon Kang Cu, Min Kyoon Shin, Ki Won Sohn, Sun I. Kim and Seon Jeong Kim, Direct Fabrication of Twisted Nanofibers by electrospinning. Applied Physics Letters 90, 263902 (2007).

Leon M. Bellan and H. G. Craighead, Control of an electrospinning jet using electric focusing and jet-steering fields, J. Vac, Sci Technol.B 24(6), Nov./Dec. 2006; 3179-3183.

Carnell, L., Siochi, E., Holloway, N., Stephens, R., Rhim, C., Niklason, L., and Clark, R., Aligned Mats from Electrospun Single Fibers, Macromolecules, 2008, 41, pp. 5345-5349.

Carnell, L.S. et al., Electric Field Effects on Fiber Alignment using an Auxiliary Electrode during Electrospinning, Scripta Materialia, (2009), 60, pp. 356-361.

* cited by examiner

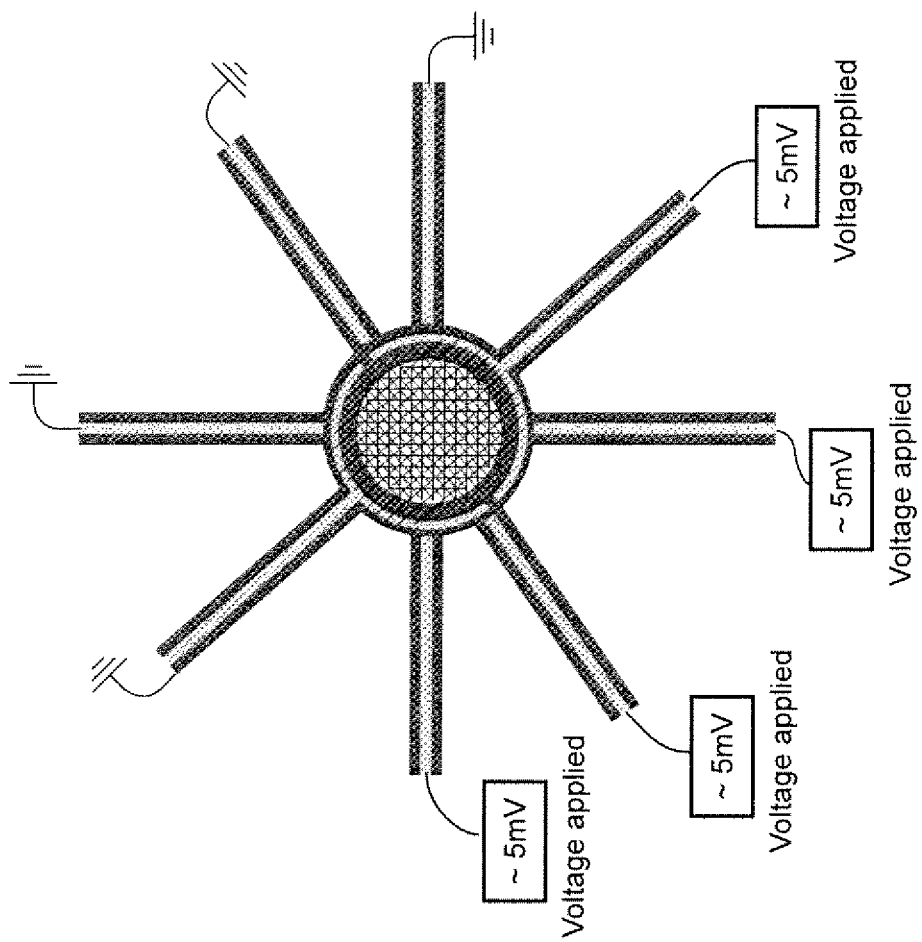

ALIGNED AND ELECTROSPUN PIEZOELECTRIC POLYMER FIBER ASSEMBLY AND SCAFFOLD

CROSS-REFERENCE TO RELATED APPLICATIONS

This patent application claims the benefit of U.S. Provisional Patent Application No. 61/286,484, filed Dec. 15, 2009.

STATEMENT REGARDING FEDERALLY SPONSORED RESEARCH AND DEVELOPMENT

This invention was made in part by employees of the United States Government and may be manufactured and used by or for the Government of the United States of America for governmental purposes without the payment of any royalties thereon or there for.

BACKGROUND OF THE INVENTION

Current scaffold designs and materials do not provide all of the appropriate cues necessary to mimic in vivo conditions for tissue engineering and stem cell engineering applications. It has been hypothesized that many biomaterials, such as bone, muscle, brain and heart tissue exhibit piezoelectric and ferroelectric properties. Typical cell seeding environments incorporate biochemical cues and more recently mechanical stimuli. However, electrical cues have just recently been incorporated in standard in vitro examinations. In order to develop their potential further, novel scaffolds are required to provide adequate cues in the in vitro environment to direct stem cells to differentiate down controlled pathways or develop novel tissue constructs. A scaffold that provides electrical stimuli in conjunction with biochemical and mechanical cues will have a significant impact on the proliferation and differentiation of stem cells and tissue constructs that can be engineered.

BRIEF SUMMARY OF THE INVENTION

In view of the foregoing, it is an object of the invention to provide a scaffold assembly and related methods of manufacturing and/or using the scaffold for stem cell culture and tissue engineering applications in order to at least partially mimic a native biological environment by providing biochemical, topographical, mechanical and electrical cues by using an electroactive material.

It is a related object of the invention to provide the ability for delivering electrical and mechanical stimuli through bioactive fibers for stem cell tissue engineering. Potential applications include stem cell therapy treatment methods such as, for example, spinal cord disorders, autoimmune diseases, and Parkinson's disease. Potential applications also include, for example, tissue engineering constructs for myocardial infarcts, blood vessels, and skin grafts.

These objects are achieved by the present invention, which in one embodiment provides an assembly for tissue engineering and/or stem cell differentiation using electrical and/or mechanical stimuli through bioactive fibers comprising at least one layer of substantially aligned, electrospun polymer fiber having an operative connection for individual voltage application.

In another embodiment, the invention provides a method of cell tissue engineering and/or stem cell differentiation, said method including the steps of providing an assembly having at least two layers of substantially aligned, electrospun polymer fiber having an operative connection for individual voltage application to each layer; seeding the assembly with a sample of cells suspended in cell culture media; incubating for an effective time period; applying an effective voltage to one or more layers; and recovering cells and/or a tissue construct.

In yet another embodiment, the invention provides a method of manufacturing an assembly for tissue engineering and/or stem cell differentiation including the steps of providing a first pre-electroded substrate surface; electrospinning a first substantially aligned polymer fiber layer onto the first surface; providing a second pre-electroded substrate surface; electrospinning a second substantially aligned polymer fiber layer onto the second surface; and, retaining together the layered surfaces with a clamp and/or an adhesive compound.

Additional objects, embodiments and details of this invention can be obtained from the following detailed description of the invention.

BRIEF DESCRIPTION OF THE SEVERAL VIEWS OF THE DRAWING(S)

FIG. 5 illustrates a schematic drawing of an assembly of four scaffold layers in a 0/90/+45/−45 configuration.

DETAILED DESCRIPTION OF THE INVENTION

Figure 1:
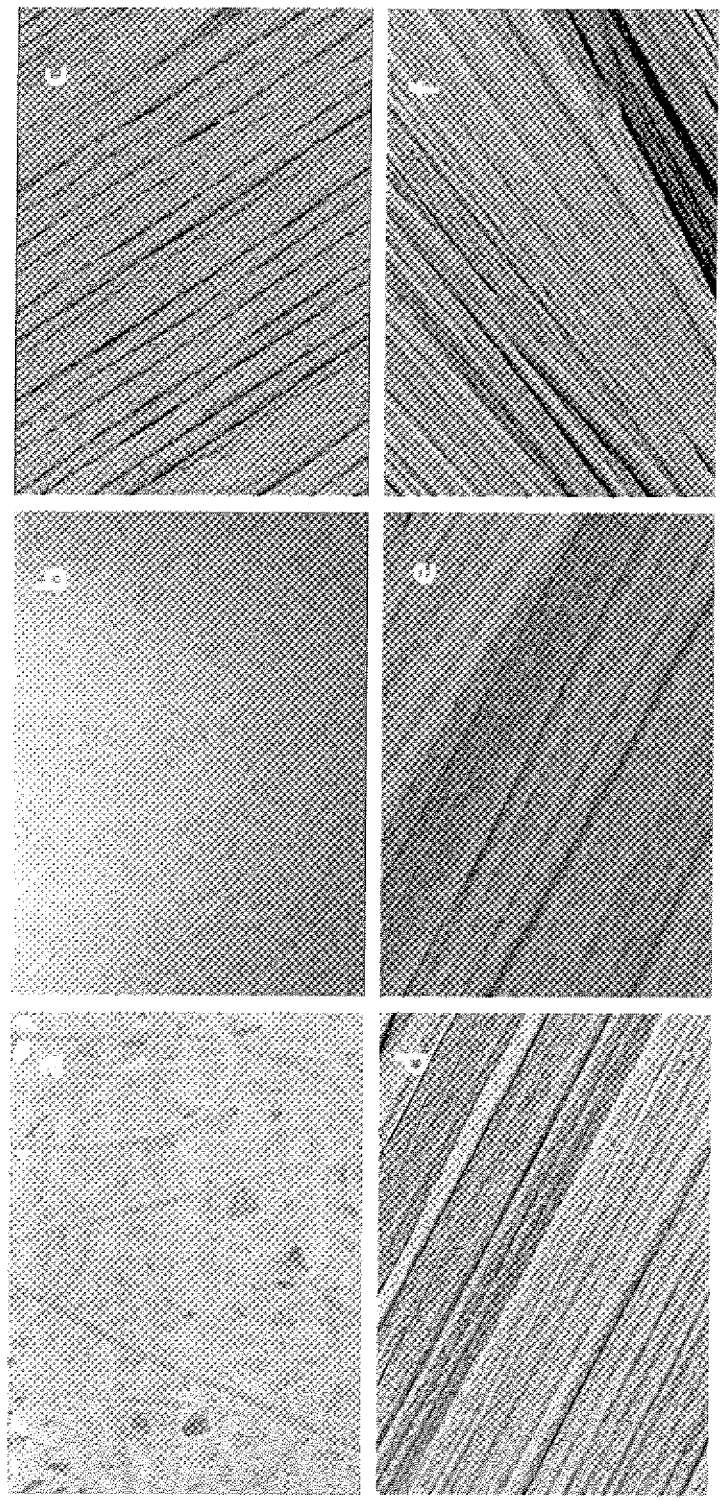
FIG. 1 illustrates SEM micrographs of electrospun PVDF after (a) non-woven image collected on a static plate without auxiliary electrode use, (b) 1-2 seconds, (c) 5 minutes, (d) 15 minutes, (e) 30 minutes, (f) 45 minutes [magnification 500× (a,c,d,f), 100× (b), and 845× (e)].

Stem cells have enormous therapeutic potential for treating a multitude of medical disorders such as Parkinson's disease, autoimmune diseases, and spinal cord injuries. An attractive feature of this therapy is the ability to inject the stem cells directly at the treatment location without the need for additional delivery mechanisms. Adult stem cells are currently used to treat leukemia and other blood and bone disorders and recently have been approved as a treatment strategy for myocardial infarcts and degenerative joint disease. Human mesenchymal stem cells (hMSCs) are adult stem cells derived from bone marrow that have demonstrated remarkable multipotency through their ability to differentiate across germ layers. A great deal of research in this area has focused on their trans-differentiation potential and the ability to direct their differentiation to specific lineages. A key component influencing the differentiation fate of stem cells is the in vitro environment in which they are cultured for expansion. This environment is comprised of a multitude of factors with the fundamentals being the selection of media, 2-D vs. 3-D scaffolds, and material considerations. Several groups have identified key differences in employing media containing serum and that free of serum with varying results. The physical culture conditions, however, remain rather elusive with numerous variables to consider such as topography, spatial dimensions, material chemistry and mechanical properties. Current scaffold designs and materials do not provide all of the appropriate cues necessary to mimic in vivo conditions. It has been hypothesized that many biomaterials, such as bone, muscle, brain and heart tissue exhibit piezoelectric and ferroelectric properties. Typical cell seeding environments incorporate biochemical cues and more recently mechanical stimuli, however, electrical cues have just recently been incorporated in standard in vitro examinations. In order to develop their potential further, novel scaffolds are required to provide adequate cues in the in vitro environment to direct the stem cells to differentiate down controlled pathways. A scaffold that provides electrical stimuli in conjunction with biochemical and mechanical cues will have a significant impact on the proliferation and differentiation of the stem cells.

The primary objectives of this invention are twofold; first, to develop a novel scaffold that provides mechanical and electrical cues that more closely mimic the cells' native environment (such as heart, brain, nerve, muscle) and second, to determine the influence of the scaffold on the differentiation potential of exemplary human mesenchymal stem cells. The inventive embodiments are segmented into four key parts; the first is the manufacture of aligned electroactive fibers that will provide the electrical and mechanical cues; the second is to create a 3-D structure from the aligned electroactive fibers and to design a scaffold that combines the 3-D aligned fiber architecture with electrical and mechanical stimulus capability; the third part is to determine the effect of topography on exemplary human mesenchymal stem cells phenotypic development by comparing 2-D vs. 3-D environments; and the fourth is to determine hMSC phenotypic development as a function of electrical and mechanical stimuli application.

In at least one embodiment, the invention involves the fabrication of electroactive polymer fibers that may comprise aliened single fibers or fiber bundles that are substantially parallel to one another. Electrospinning was used to yield fibers that can exhibit crystalline structures in polar form due to the strong electric field. And since aligned fibers are crucial in directing stein cell differentiation, the electrospinning process was modified to generate highly aligned electroactive fibers in situ using an auxiliary electrode to focus the electric field. For more details on an exemplary method and system for aligning fibers during electrospinning, please see application Ser. No. 12/131,420, which has published as US 2009/0108503 A1, which is herein incorporated by reference.

One of the specific aims of this invention is to fabricate an exemplary scaffold that confirms the effect of topography and architecture on the differentiation of exemplar) hMSCs. Such a scaffold design has not been demonstrated previously and this invention is significant because topography is known to play a critical role in attachment differentiation and proliferation of hMSCs. Although hMSCs are discussed in detail, certain inventive embodiments include other types of stem cells, e.g. induced pluripotent and/or embryonic stem cells. Research performed by Yim and Hu et. al. demonstrated the significant influence topographical cues have in directing the differentiation of hMSCs. It was observed that hMSCs respond to features in the nanometer and micrometer range. The formation of the extracellular matrix has been shown to occur on the nanometer level making this an attractive dimension. Other groups have investigated the effect of surface chemistry on the attachment, proliferation and differentiation of hMSCs. Engler et. al. reported that a material's elastic modulus alone is capable of directing stem cell differentiation. They found that collagen production was significantly reduced when hMSCs were cultured on a 'soft' matrix compared to a 'hard' matrix intended to mimic the differences between biomaterials such as the brain and bone. In addition to topography, the architecture contributes considerably to the overall success of the scaffold. A scaffold comprising a three dimensional environment more closely mimics native surroundings than one constructed from two dimensions. There are two predominant scaffold constructs that provide a three dimensional environment, gels and fibers. Gels produced from collagen, fibrin, gelatin, alginate, and more recently thermoresponsive polymers demonstrate differing results compared to conventional two dimensional systems when used to culture hMSCs. Scaffolds fabricated from fibers with diameters ranging from nanometers to micrometers have also been investigated extensively as three dimensional constructs. Interesting results have been observed with this type of environment. One study compared the effects of a three dimensional gel environment to a fibrous scaffold and found vastly differing results between the two. Another scaffold was designed to mimic native cartilage by employing a composite structure manufactured to emulate the mechanical properties. A key issue confronting three dimensional scaffolds to date is control over the porosity. Porosity is vital to the health and maintenance of the cells in culture. If the porosity is insufficient, the cells will not receive adequate nutrients and may undergo hypoxia. One way to prevent this is to use aligned fibers to control porosity. Aligned fibers have been investigated extensively and shown to promote cell alignment and attachment due to their high surface to volume ratio. Studies suggest that a fibrous structure plays a fundamental role in the modeling of the extracellular matrix and overall gene expression.

Some embodiments of the invention involve electroactive polymer fibers, and in preferred embodiments, the polymer fibers used are composed of polyvinylidene fluoride (PVDF). PVDF is a commercially available polymer used in a variety of areas ranging from aerospace, medical, and automotive to common household applications. It is a crystalline material capable of assuming four different phases ($\alpha$, $\beta$, $\gamma$, $\delta$) depending upon processing and post-processing conditions. The $\gamma$ and $\delta$ phases are quite uncommon and will not be examined for this study. The most common form is the $\alpha$-phase. The crystalline structure is in a trans-gauche (TGTG) configuration. When the material is mechanically stretched its crystalline form is altered to assume an all-trans configuration, which renders it electroactive due to alignment of the dipoles present in the structure. Subjecting the mechanically stretched material to an electric field further increases the dipole alignment in the crystalline structure and enhances the electroactive properties. This highly polar form is classified as the $\beta$-phase and is the desired state due to its unique electroactive properties. Electroactive PVDF is in a class of materials that exhibit piezoelectricity, i.e. a mechanical strain is elicited with the application of a voltage and conversely, an electrical signal is produced with the application of a mechanical strain. It is also pyroelectric, exhibiting an electric charge as a function of temperature. This is typically referred to as ferroelectric. PVDF poses an exciting possibility for cell culture studies for at least two reasons. First, the piezoelectric properties of the $\beta$-phase allows for direct application of electrical and mechanical stimuli to the cells. Second, its pyroelectric property resulting from an applied temperature is novel. Thermally stimulated current (TSC) data indicates that PVDF generates a slight current equivalent to approximately 2.2E-10 A/m2 when subjected to standard cell culture conditions of 37° C. This property was included in the analysis during the topographical portion of the study. PVDF has been considered for a wide range of biomedical applications such as sutures and surgical meshes due to its inert chemistry and good biocompatibility.

Exemplary human mesenchymal stem cells (hMSCs) have generated an enormous amount of interest due to their multipotency, the fact that they are non-controversial and they do not form teratomas. hMSCs have demonstrated multipotent potential through their ability to trans-differentiate. Several research groups have reported success in directing hMSCs to differentiate into adipocytes, chondrocytes, osteoblasts, neurons, cardiomyocytes and muscle. There is considerable debate as to whether hMSCs actually trans-differentiate or are coerced into specific lineages by fusion with mature cells present in their surroundings. Research by Engler et. al. has provided additional clarification surrounding this highly controversial topic with their discovery on the multipotent potential of hMSCs based on the modulus of the scaffold. Their study revealed a passive response of the hMSCs to the microenvironment which is presumed to be indicative of a multipotent stem cell.

Although hMSCs trans-differentiation potential has sparked a great deal of debate among the research community, there is no dispute regarding the multipotent potential of hMSCs and their ability to be considered for therapeutic applications. In fact, hMSCs are an ideal research line because they are not controversial since, they are derived from bone marrow and in many instances, they can be autologous, eliminating immunorejection concerns. Embryonic stem cells, while undoubtedly pluripotent, have generated a significant degree of controversy primarily over sourcing. It will be challenging for human embryonic stem cells to be considered for clinical applications in the near term for this reason and also because they are extremely difficult to control, often giving rise to tumor formation.

In order to direct stem cell differentiation in vitro, it is necessary to provide the appropriate cellular cues and environment. This includes biochemical, mechanical and electrical signals that emulate the native cellular environment. Typically, cells are seeded in a tissue culture treated polystyrene dish and provided with biochemical cues to guide them down a specific lineage. This has demonstrated moderate success, but does not emulate the cells native environment. Researchers have recently begun to investigate the effects of mechanical properties on the growing cells. They have demonstrated that providing a mechanical environment similar to a cell's native area contributes significantly to the lineage pathway chosen. Another group of researchers has shown that providing electrical signals to embryonic stem cells results in a much larger number of cells exhibiting markers for a neuronal pathway. In order for stem cell therapy to become viable, cells must be harvested, dissociated into individual cells and expanded ex vivo. Stem cells that can be differentiated into a preferred lineage and expanded down that pathway possess the ability to provide great therapeutic potential for numerous health disorders, hMSCs are currently being considered for treatment in Parkinson's disease and other neural disorders due to their demonstrated ability to trans-differentiate or by creating a favorable environment through the release of soluble factors.

There are a multitude of neurological and immune disorders for which cures remain elusive in the research community despite society's best efforts. In order to treat these conditions, new methods and clinical treatments must be considered. Technology has brought about substantial medical advances through the introduction of state-of-the-art diagnostic equipment and the ever changing drug therapies available. It is necessary to step around some of the current barriers to treatment and examine new options. Stem cell therapy offers boundless potential for improving the quality of life for millions of individuals, possibly even offering cures for diseases previously unattainable. Hence, despite numerous obstacles, research into hMSCs for stem cell therapy remains robust.

Inventive materials selected included PVDF, which was selected for its unique electroactive properties and its potential for biocompatibility. A fluorinated polyimide, CP2, was also selected and synthesized from 2,2'-Bis(3,4-dicarboxyphenyl) hexafluorpropane dianhydride (6FDA) and 1,3-bis (4-aminophenoxy)benzene (APB) and was included to compare to the PVDF due to its potential for biomedical applications. The biocompatibility of electroactive PVDF was verified by performing a live/dead assay and examining the metabolic activity compared to standard tissue cultured polystyrene (TCPS) and a polyimide, CP2. The cells demonstrated good spreading and morphology on both film surfaces. A WST-1 assay confirmed the metabolic activities of PVDF and CP2 were comparable to TCPS indicating good biocompatibility between hMSCs and PVDF. Since the surface of the material plays a critical role in the cell attachment and spreading, we analyzed the films for functional groups present, surface roughness, and surface energy. FTIR-ATR results indicated the presence of primary aliphatic —OH functional groups for PVDF by the peaks present at 1066 cm-1 and ~3600 cm-1. Aliphatic —COOH functional groups were identified in the spectra for CP2 by the broad —OH stretching region from 2500-3500 cm-1 and peaks present at 1072 cm-1, 1239 cm-1 and 1720 cm-1. It has been reported that —OH and —COOH functional groups play a significant role in cell attachment and proliferation. Several research groups have attempted to add these functionalities to their materials to enhance these features and promote proliferation.

Contact angle measurements were performed on each film surface using media warmed to 37° C. and found to be 67.34° for PVDF and 78.68° for CP2 at equilibrium indicating the surfaces were hydrophilic. The surface energy was calculated based on the equilibrium contact angle observed and was found to be 34.91 dynes/cm for PVDF and 26.02 dynes/cm for CP2. These values are quite low for a hydrophilic material however, the surface roughness is not included in the theoretical equation although it contributes significantly to the wettability of the surface. The average surface roughness for each material was found to be 0.069 µm for PVDF and 0.009 µm for CP2 indicating sufficient roughness to promote adhesion at the cellular level. The results were illustrated with images obtained using an optical profilometer.

Several researchers have reported a significant reduction in electroactive properties over a period of time when exposed to in vivo conditions. Therefore, an in vitro degradation study was performed on PVDF to ensure the material properties were not changed as a result of long term exposure to the environment.

The mechanical properties were measured on five PVDF samples and averaged over the degradation period. There was very little change over the 28 day period with overall about 4% difference between the baseline and the last day for the ultimate break stress, 7% difference in the elongation and about a 5% difference in the modulus. There was not a reportable difference in the piezoelectric properties over the 28 day period as indicated by the thermally stimulated current method.

The electrospinning manufacturing process is a simple and versatile process that can be used to fabricate micro and nanofibers from polymer solutions and melts. The process has typically produced random nonwoven mats and was modified for this study to develop aligned fibers for a more controlled architecture. The set-up incorporates an auxiliary electrode that creates a dipole field and directs the electrospun fiber to a collector without the typical whipping and bending instabilities observed in other systems. The fiber continues to be pulled along the dipole field over time and can be directed at an angle due to the repositioning of the auxiliary electrode. SEM micrographs illustrated in FIG. 1 demonstrate the degree of alignment achieved for various time periods ranging from 1 second to 45 minutes.

The crystalline structure of PVDF aids in determining the overall properties of the resulting polymer, specifically, the piezoelectric state. A common technique to induce the β-phase is to subject the α structure to mechanical stretching and a high electric field which results in orientation of the dipoles within the crystalline structure. Electrospinning incorporates both of these features; first by mechanically drawing the fiber from the spinneret to the collector and second by creating a strong electric field which the fiber is expelled through. The results from electrospinning a pure α-phase powder from a solution of 50/50 DMF:Acetone indicate a transition to the β-phase occurred based on peak shifts illustrated in the x-ray diffraction (XRD) diffractogram. When examining the material using XRD, there are two primary peaks indicating the starting crystalline form is in the alpha phase. A shift of $2\theta$ to $20.6°$ indicates 200/110 reflections of the β-phase whereas the two shoulder peaks at $2\theta=18.25°$ and $19.8°$ represent the 020 reflection of the α-phase. The peak around $2\theta=26.63°$ is representative of the α-phase. This peak was not present in any of the processed forms present in the diffractogram indicating a shift from the α-phase to the β-phase occurring. The electrospun nonwoven PVDF showed a peak shift around $2\theta=28.57°$ suggesting it has not fully transitioned to the β-phase. An additional peak around $2\theta=36.14°$ represents the 200 plane and is another indicator that the β structure has been formed.

Fourier transform infrared spectroscopy (FTIR) with attenuated total reflectance confirmed the transition to the β-phase by a change in the vibrational bands characteristic of the α-phase at 615 cm-1, 766 cm-1 and 795 cm-1 and the presence of a vibrational band at 840 cm-1. Differential scanning calorimetry (DSC) results for the electrospun aligned fiber depicted a melting point of approximately 160° C. on the first heat. Subsequent quenching and a second heat indicated a shoulder peak present at 155° C. and 160° C. which was indicative of the two crystalline phases present, further demonstrating the crystalline β-phase transformation. The melting temperature for the electrospun aligned fibers was lower than that for the poled film (165° C.). There are several factors that may contribute to the slight decrease. The number of head-head and tail-tail chain configurations will play a role in the overall melting point as will the percent crystallinity and the amount of α-phase and β-phase present. The presence of a shoulder peak in the poled film and its absence in the pure powder further signifies the presence of both phases.

A modified Rheovibron was used to measure the d31 piezoelectric constant of a fibrous mat electrospun from PVDF for 45 minutes. Gold electrodes were deposited on both sides of the mat and measurements were performed by applying a tensile load of 35 g and measuring the d31 constant as a function of frequency and temperature. Results were obtained for frequencies at 1 Hz, 10 Hz, 20 Hz and 100 Hz over a temperature range of 23° C. to 50° C. A value for d31 was obtained, thus validating the rationale that electrospun aligned PVDF fibers are poled in-situ during the electrospinning process.

As discussed earlier, topography plays a significant role in cell attachment, differentiation and proliferation of exemplary hMSCs. In order to determine the effect of fiber morphology on the culture of hMSCs, the inventors performed cell culture studies on films of the same material to be examined in fiber form. Preliminary results from examining the cells after 7 days and 14 days in culture indicate advanced cell structure by the presence of intermediate filament vimentin. A strong presence of beta III tubulin (TUJ1), an early stage neuronal marker, was present for all of the materials and MAP2 was present in the group conditioned with retinoic acid and PVDF. Retinoic acid has been identified as a chemical agent that induces the neuronal lineage in culture. Reverse transcriptase PCR was performed on mRNA extracted from the samples after 7 days and 14 days in culture. Gel electrophoresis staining indicated the upregulation of Oct 4, a marker typically present in embryonic stem cells, for the CP2 polyimide coverslip, coverslip with retinoic acid and TCPS after 14 days in culture. Genes corresponding to C-kit were present in PVDF and coverslip. All of the material samples expressed SOX 9, an early marker for chondrycyte formation and alpha-fetoprotein (AFP). AFP is a protein expressed during early endoderm development and has been shown to express in hMSCs during hepatocyte differentiation. PVDF also indicated the upregulation of MAP2 after 14 days in culture. This indicates there may be something happening on the cell signaling level with PVDF, perhaps related to the pyroelectric behavior, since MAP2 is a gene expressed during neuronal development. The expression of both endoderm and mesoderm markers suggested a mixed population of cells present. Gel electrophoresis data for the 7 day films did not readily express any of the genes the inventors probed for although the housekeeping genes, beta actin and GADPH, were clearly observed.

In order to determine the effect of PVDF fibers on the culture of hMSCs, scaffolds were manufactured from both CP2 polyimide and PVDF. The fibers were electrospun directly onto rings to be used in culture and affixed using cyanoacrylate. The fibers were deposited in a configuration to allow the greatest degree of porosity while maximizing cell attachment. Three different aligned fiber configurations were examined. The 'standard' configuration was composed of fibers having average diameters of approximately 8 μm, the 'fine' sample fiber diameters were on the order of 1 μm and the 'mixed' sample consisted of a basement layer of fine fibers followed by three additional layers of standard sized fibers. The lay-up was in a 0/90/+45/−45 arrangement for each sample type. A sample comprised of a nonwoven collection of fibers was used to assess the impact of aligning the fibers. Initial studies examined the effect of this architecture by performing live/dead assays on fiber scaffolds manufactured from CP2.

Figure 2:
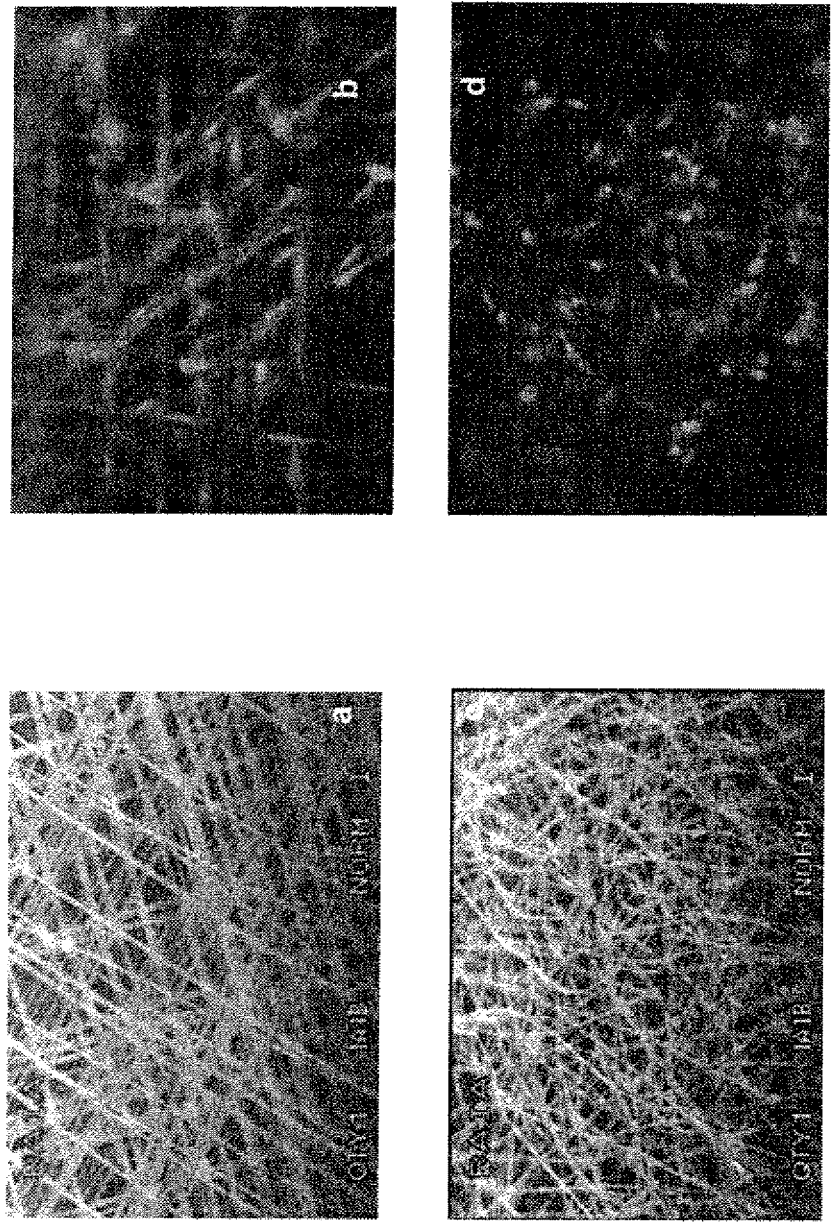
FIG. 2 illustrates scaffolds fabricated from CP2 polyimide with (a) optical image of 4 layer aligned fibers [mag. 10×], (b) live/dead assay results on aligned fibers, (c) optical image of nonwoven fibers [mag. 10×], and (d) live/dead assay results on nonwoven fibers.
Figure 3:
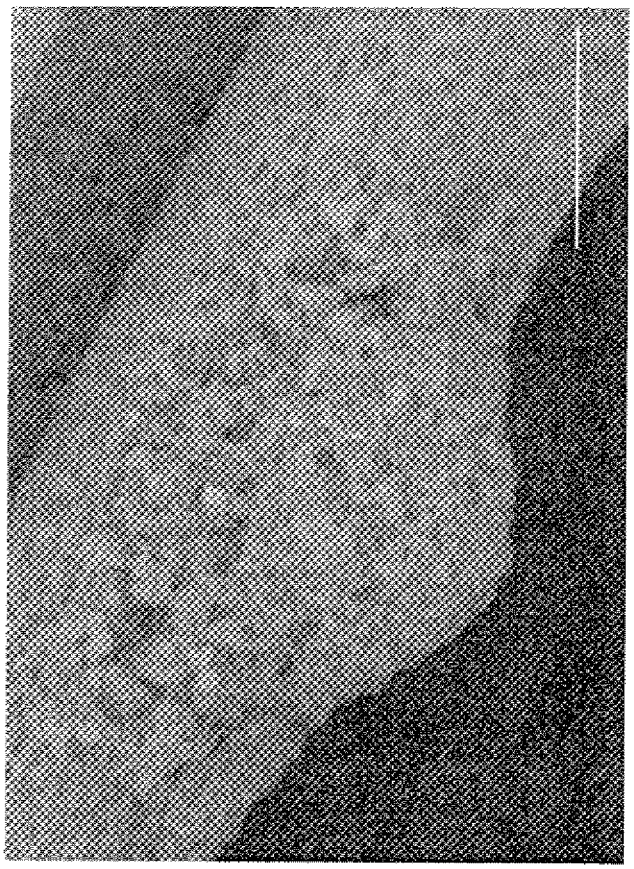
FIG. 3 illustrates SEM micrograph of a cell attached to the surface of a CP2 fiber.

The results are illustrated in FIG. 2. It is apparent from the results, which indicated the presence of some dead cells, that the nonwoven scaffold either did not allow the appropriate nutrients to diffuse through the scaffold or that the cells could not penetrate the scaffold for proper attachment. The aligned fibers, although quite auto-fluorescent, provide a good environment for cell culture as can be observed by the cell attachment along the length of the fibers and throughout the multiple layers. An SEM micrograph depicting a dehydrated cell attached to a CP2 fiber is illustrated in FIG. 3. Gel electrophoresis results indicated the presence of Sox 9, a marker for chondrocyte formation, for each of the CP2 fiber sizes and architectures examined after 7 days in culture. Immunostaining of CP2 aligned fibers for vimentin, actin and the nucleus revealed a well organized cell. The cells showed substantial alignment along the fibers. The mixed fibers did not display a cell structure as organized as those observed on the standard and fine fibers. The nucleus was much more elongated on the fine fibers compared to the standard fibers. This suggests the cell was sitting on top of the standard size fibers since they are roughly the same size and the cell was elongating and perhaps wrapping around the fine diameter fibers in order to attach.

PVDF fibers were also electrospun onto rings, in the configuration described above for CP2, and affixed with cyanoacrylate, cultured for 7 days and stained for vimentin, actin and the nucleus. The cells were observed with confocal microscopy to attach to the fibers. The nucleus was elongated along the length of the fiber illustrating the influence of topography on the cell morphology. It was also observed that what appears to be two cells attached to different fibers bridged across the fibers to contact one another.

Figure 4:
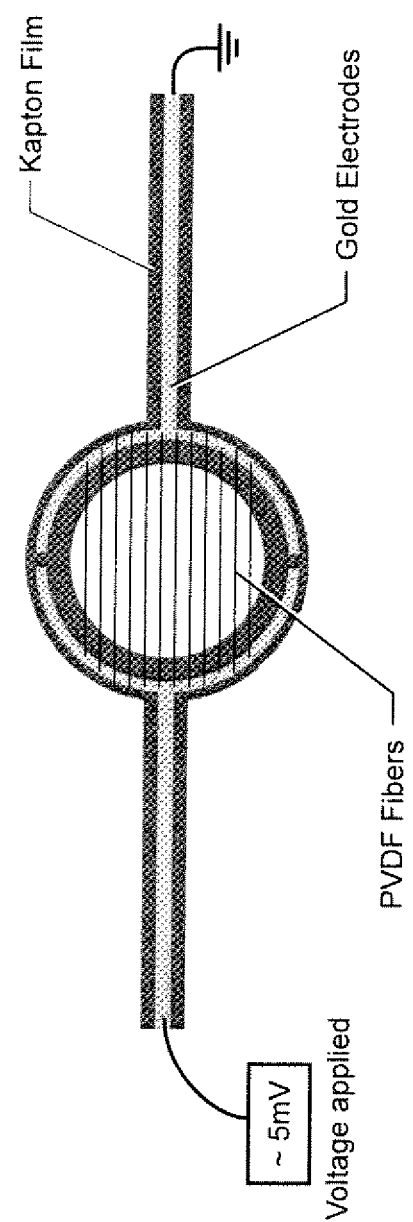
FIG. 4 illustrates a schematic drawing of an exemplary scaffold with PVDF fibers electrospun directly onto a pre-electroded surface.

In at least one embodiment of the invention, an assembly for tissue engineering and/or stem cell differentiation is provided using a 3-D scaffold to apply electrical stimuli. In one embodiment, at least several factors were considered in the design of the 3-D scaffold in order to apply electrical and mechanical stimulation. These included the geometry, substrate, electroding, adhesive, clamp fixture and fiber deposition. An exemplary 3-D scaffold was designed such that PVDF fibers could be electrospun directly onto a pre-electroded (FIG. 4) surface minimizing the potential for shorting by electroding the fibers post-processing. The plan in this instance was to manufacture four layers independently, place them in a 0/90/+45/−45 configuration (FIG. 5) and retain them with a specially designed clamp. This allowed for the direct stimulation of each layer independently. Cell culture studies were performed on the scaffolds with the application of voltage to each layer.

Accordingly, each substrate layer was fabricated using Kapton™ polyimide (DuPont) by laser cutting a 28 μm sheet of film. Gold electrodes were evaporated on each substrate. Gold was chosen as the electrode material due to its inert properties and excellent biocompatibility. Devcon™ silicon adhesive was used to glue the electrospun fibers to the electroded substrates. Each layer was fabricated separately, glued and allowed to air dry for a minimum of 48 hours. The four separate layers were joined together using the silicon adhesive and allowed to dry for a minimum of 48 hours prior to cell culture.

A clamp was designed to hold the four layer scaffold construct together and keep it suspended from the bottom surface and allow for each layer to be stimulated independently or simultaneously. A grooved portion provided space for the flexible leads to extend outside of the culture area and the top piece secured the scaffold together by fitting snugly into the grooved piece. The clamp was fabricated from acrylic polymer resin using the stereolithography rapid protyping process.

In order to maintain the existing architecture for comparison purposes, a similar design will be employed with one end of the substrate fixed and the free end mechanically extended in order to strain the PVDF fibers. The substrate will be cut on each side in order to obtain direct straining of the fibers without the influence of the substrate. Mechanically straining the fibers will elicit an electrical signal that is expected to have a significant impact on the differentiation and proliferation of the hMSCs over time.

Exemplary human mesenchymal stem cells were obtained from Tulane University. A single male donor was used throughout the study to prevent donor-donor variables. hMSCs were cultured in alpha minimum essential medium (αMEM) with L-glutamine, but without ribonucleosides or deoxyribonucleosides (Invitrogen/GIBCO), containing 16.5% fetal bovine serum, premium select, hybridoma qualified, not heat inactivated (PBS, Atlanta Biologicals), 200 mM in 0.85% NaCl of L-glutamine (Invitrogen/GIBCO), 100 units/ml penicillin and 100 μg/ml streptomycin (Invitrogen/GIBCO). Cell culture medium was filtered through a sterile filter unit. Cells were plated at an initial density of approximately 350 cells/cm$^2$ in a 15 cm dish and incubated at 37° C. with humidified 5% $CO_2$. Media was replenished every three days. Cells were passaged after reaching approximately 80% confluence by aspirating media, washing 1× with phosphate buffered solution (PBS, Invitrogen) and lifting with 0.25% Trypsin and 1 mM ethylene diamine tetracetic acid (EDTA) in Hank's balanced salt solution (Invitrogen/GIBCO) for 1-3 minutes at room temperature. After incubation in Trypsin/EDTA, 5 ml of cell culture media was added and the mixture was transferred to a 15 ml conical centrifuge tube. The cells were centrifuged for 10 minutes at 450×g at room temperature. The supernatant was aspirated and the cell pellet resuspended in 1.0 ml cell culture media. Cells were counted by adding 10 μl 0.4% Trypan Blue solution to 10 μl of cell suspension and dispersing them onto a hemocytometer. Cells were seeded onto scaffolds between passages 2-5 at a density of approximately 125,000 cells/cm$^2$. Attachment of the cells to the scaffold was promoted by seeding an initial volume of 250 μl of cell suspension on each scaffold and allowing it to incubate at 37° C. with humidified 5% $CO_2$ for a minimum of one hour. After the initial incubation period, an additional volume of 3-4 ml of cell culture media was added to each well and the scaffold were placed back in the incubator at 37° C. with humidified 5% $CO_2$ for 7 days. Media was replenished every three days. Electrical leads clamped to the flexible leads of the scaffold were attached to a power supply and a 9 mV/cm stimulus was applied to each scaffold layer after approximately 24 hours post-seeding at a frequency of 500 mHz.

In order to determine an exemplary minimum voltage required to cause an effect on the calcium channels, a preliminary calcium imaging experiment was performed using a Fluo-4 NW (no wash) assay (Molecular Probes). PVDF and CP2 polyimide films were examined. Films were laser cut to provide a flexible lead and Au electrodes were evaporated on the surface in order to attach wires to the substrates. hMSCs were seeded on PVDF and CP2 films at a density of 5000 cells/cm$^2$ and allowed to incubate for 24 hours at 37° C. in humidified 5% CO2. A 250 mM stock solution of probenicid was prepared by adding of assay buffer to probenicid and vortexing until dissolved. The dye loading solution was prepared by adding 10 mL assay buffer and 100 μL probenicid stock solution to Component A and vortexing for 1-2 minutes. A 1 μM acetylcholine (AcH) (Sigma-Aldrich) sample was prepared in buffer. To prepare for imaging, media was removed from the wells and the samples were washed 2× with PBS. A volume of 1 mL, of dye loading solution was added to each sample and the samples were incubated at 37° C. in humidified 5% CO2 for 30 minutes. The samples were placed under an upright fluorescent microscope (Zeiss AxioObserver) fitted with a heated stage. Wires were attached to the flexible electrodes protruding outside of the chamber. The voltage supply (Keithley) was monitored using an oscilloscope (Wavetek). Data were recorded for a period of 2 minutes prior to the application of stimuli. AcH was added after several minutes of baseline data collection and served as a positive control. Power was applied to the substrate and recorded for several minutes. Data was obtained and post-processed using Metamorph software (Zeiss). The average fluorescence intensity for a minimum of 7 cells was plotted as a function of time.

Results from the live cell calcium imaging study indicated that application of 9 mV/cm of a direct current electric field was sufficient to elicit a response in the cells. The addition of AcH showed a peak intensity of about 600 while the CP2 film with 9 mV/cm direct current electric field applied had an intensity of around 1100, nearly two times the results obtained with AcH. The PVDF film peaked around 625, similar to the results obtained using AcH to stimulate the Ca+ channels. Spontaneous Ca+ signals were observed in the PVDF film prior to the application of 9 mV/cm direct current electric field.

The proliferation of cells was analyzed using EdU Click-iT™ Imaging Kit (Invitrogen). Cell culture was performed as described above. Briefly, hMSCs were seeded on scaffolds and in a 6 well tissue culture dish at a density of 200,000 cells. After 24 hours in culture, EdU was added to the media at a concentration of 10 µM. After 3 days in culture, media was replenished with fresh media containing 10 µM of EdU. After 7 days, the samples were removed, fixed with 4% PFA (Sigma-Aldrich) for 15 minutes at room temperature then washed 2× with PBS containing 3% bovine serum albumin (BSA, Sigma-Aldrich). After the wash was removed, the samples were incubated for 20 minutes at room temperature in 0.5% TritonX-100 in PBS. The reaction cocktail was prepared by mixing 1.8 mL 1× Click-IT reaction buffer, 80 µL $CuSO_4$, 5 µL Alexa Fluor azide, and 200 µL reaction buffer additive. The permeabilization buffer was removed and the samples were washed 2× with PBS containing 3% BSA. The wash was removed and the Click-iT reaction cocktail was added to each sample. The samples were incubated for 30 minutes at room temperature protected from light. The reaction cocktail was removed and the samples were washed with PBS containing 3% BSA. Each sample was washed with PBS prior to DNA staining. A Hoechst 33342 (1:2000) was added to each sample and incubated for 30 minutes at room temperature protected from light. The samples were washed 2× in PBS and mounted to coverslip with gel mount (Invitrogen). The samples were imaged using confocal microscopy. A minimum of 400 cells were counted.

Proliferation results for the PVDF fiber stimulated scaffold and TCPS indicated the stimulated scaffold had 10% greater incorporation of EdU compared to TCPS, with 33% EdU-positive cells in the stimulated fiber scaffold compared to 23% on TCPS.

Immunostaining was performed. After 7 days in culture, samples were washed with PBS and fixed in 4% paraformaldehyde for 15 minutes at room temperature. Following fixation, the samples were washed 2× in PBS. A solution containing 0.25% Triton-X 100, 1% bovine serum albumin and 10% goat serum was prepared in PBS. Samples were probed for primary antibodies including Vimentin (1:200. Sigma-Aldrich), F-Actin (1:50, Molecular Probes), TUJ1 (1:500, Covance), MAP2 (1:400, Sigma-Aldrich), and DAPI (1:5000, Molecular Probes) and allowed to incubate for 2 hours at room temperature. The samples were washed 3× with PBS and secondary antibodies of Alexa-Fluor conjugated goat anti-mouse (1:200) and goat anti-rabbit (1:200) were added and allowed to incubate for a minimum of 1 hour at room temperature covered with aluminum foil to protect them from light. The samples were washed 2× with PBS and mounted to coverslips using Gel-mount (Invitrogen). The samples were imaged using laser scanning confocal microscopy.

Immunostaining results from examining the cells after 7 days in culture on PVDF fibers stimulated with 9 mV/cm direct current applied field indicate advanced differentiated cell morphology by the presence of intermediate filament vimentin. The cells attached to multiple layers of the scaffold with the nuclei highly aligned along the fibers. Vimentin appeared to be forming a network across the fibers similar to what was observed in the culture on CP2 and PVDF fibers. Neuronal markers MAP2 and TUJ1 were evident.

Western Blot was performed. Determining the protein concentration was performed. After 7 and 14 days in culture, protein was extracted from the cells attached to the scaffolds by placing the dish on ice, aspirating the media, washing 1× with PBS and adding 250 µl RIPA buffer (Pierce) containing 1:100 Halt Protease Inhibitor (PI, Pierce) cocktail (100 mM AEBSF.HCl, 80 µM Aprotinin, 5 mM Bestatin, 1.5 mM E-64, 2 mM Leupeptin, 1 mM Pepstatin A) to prevent protein degradation. The lysis buffer containing the extracted proteins was transferred to a 2 ml microcentrifuge tube and stored at −80° C. until use. The protein concentration was quantified using the bicinchoninic acid (BCA) kit (Pierce). A standard curve was generated using BSA. The Gel was prepared, loaded and run. The protein sample containing 2× Laemmli buffer (Sigma-Aldrich) was heated at 95° C. for 5 minutes and centrifuged briefly prior to loading. Polyacrylamide Ready Gels (Biorad) having a range from 5-20% and 30 µl wells were placed in the electrophoresis chamber. The chamber was filled with 1×SDS-PAGE running buffer consisting of Tris base (25 mM, pH 6.8), Glycine (192 mM) and SDS (0.1%) in deionized water. The standard was made from Precision Plus Protein Kaleidoscope Standard (Biorad) and 5.5 µl was loaded into the first well of each gel. 10 µg of protein was loaded in the gel. The gel was run at 180 V for 55 minutes. The Gel was transferred. The gel was removed and placed over a pre-wetted nitrocellulose transfer membrane. The gel and transfer membrane were assembled and placed in the chamber with the gel facing the anode and membrane facing the cathode. An ice block was added to the chamber and it was filled with transfer buffer consisting of Trisbase (25 mM), Glycine (192 mM) and Methanol (20%). The set-up was transferred to the cold room and run for 90 minutes at 80 V.

Primary and Secondary Antibodies were added. A 100 ml solution of 5% nonfat milk (Biorad) in 1×TBS (50 mM Tris pH 8.0, 150 mM NaCl) containing 0.1% Tween 20 (Sigma-Aldrich) was prepared for blocking. The transfer membrane was removed from the chamber, stained with Ponceau S nonspecific protein stain (Sigma-Aldrich) and cut using a razor blade at the expected molecular weight ranges for each protein being probed. The samples were placed in the milk solution to block for a minimum of one hour. The primary antibody was added according to the following dilutions: MAP2 (1:500), Nestin (1:500), GAPDH (1:200), Actin (1:6000), MyoD (1:200), Myogenin (1:200) and GFAP (1:500). The samples were incubated in the primary antibody overnight in the cold room on a rocker. The samples were then washed 3× with TBS containing 0.1% Tween 20 for 5-10 minutes each wash. The secondary antibodies, Mouse-HRP (horseradish peroxidase) (1:5000, Novagen) and Rabbit-HRP (1:3000, Biorad), were added to a 5% milk (Biorad) solution. The samples were incubated in the secondary antibodies for a minimum of one hour. The samples were then washed 3× with TBS containing 0.1% Tween 20 for 5-10 minutes each wash.

Chemiluminescent Detection was performed. The antibody detection solution was prepared by mixing component A and B in a 40:1 ratio. The samples were prepared for imaging by placing Saran wrap over a piece of cardboard and reassembling each membrane on the Saran wrap. The antibody detection mixture was added to the membrane and allowed to incubate for 5 minutes in the dark. The detection mixture was carefully blotted to remove any excess and Saran wrap was placed over the top of each membrane. The membrane was exposed to the camera without a filter for two time periods, 5 minutes and 10 minutes in the Alpha Innotech Fluorochem Imager. The data was analyzed using the AlphaEase FluorChem software by normalizing the protein bands to the housekeeping protein GAPDH.

Western blot analysis showed the expression of MAP2 (72 kDa) protein in stimulated PVDF fibers. Protein content was quantified by normalizing to the housekeeping protein GAPDH. In comparison to the results obtained for CP2 and PVDF fibers there was much lower expression of MAP2 (72 kDa) protein for both the CP2 and PVDF fibers compared to the PVDF stimulated fibers.

In summary, culturing hMSCs on an exemplary scaffold designed to provide electrical stimulation succeeded in demonstrating the formation of an organized cytoskeleton. In contrast, Titushkin et al. reported that the application of 2 V/cm direct current electrical stimuli to hMSCs resulted in membrane detachment from the cytoskeleton. There are several possible reasons for the differences observed. The field applied in our design was much lower at 9 mV/cm compared to Titushkin's. Furthermore, the field applied to the PVDF fibers was used by the PVDF fibers to stimulate the dipoles in its crystalline structure resulting in an indirect effect on the cells. One could think of this as the PVDF fibers enabling the conversion of the applied voltage to a mechanical strain on the fibers. Although this electric field was substantially lower than what is required to elicit a mechanical response in the PVDF at the macroscale, any movement in the molecular structure most likely can be felt by the cells due to their highly sensitive nature.

The proliferation results indicate the stimulated PVDF fibers incorporated about 10% more EdU than the TCPS. Previous studies investigating the proliferation of hMSCs when cultured on nanotopography show a decrease in the proliferation compared to TCPS due to the influence topographical cues have on the differentiation of the cells. One explanation for our results may be due to the 3D architecture of the scaffold. The cells attached to the multiple layers had access to more surface area for proliferation compared to a 2D environment. A high seeding density may have also caused reduced proliferation in TCPS since hMSCs are contact inhibited cells, i.e. they stop dividing when they reach confluence.

The results obtained for protein expression indicate the stimulated PVDF fibers are producing MAP2 protein. Immunostaining for this protein confirms the presence although at a low level. MAP2 has several isoforms associated with it resulting in expression at different molecular weights, 72 kDa (MAP2c), 100 kDa (MAP2d) and kDa (MAP2a). The PVDF stimulated fibers expressed a wide band at 72 kDa but no presence of the other isoforms was detected. This may indicate the differentiation process is occurring at a much slower rate which correlates well with the enhanced proliferation observed. CP2 and PVDF fibers showed strong bands for the isoform at 100 kDa and all materials showed very weak or no presence at 239 kDa. The precise role of each isoform has been described by Kavallaris et al. as having distinct cellular functions. They explain that in the early stage of development and differentiation, lower molecular weight isoforms MAP2c and MAP2d form. The higher molecular weight isoforms, MAP2a and MAP2b, are found exclusively in dendrites of neuronal cells with MAP2a being the highest molecular weight found in late stage development and MAP2b present in embryonic and adult stages. MAP2d is expressed as alternative splicing of MAP2, is developmentally regulated and found in neuronal cell bodies. MAP2c has been expressed in dendrites, axons and glial cells and has been found to express at high levels during early brain development. This isoform is typically replaced by higher molecular weight isoforms, however, it has been found to remain in the olfactory system and the retina. Since MAP2c is found in all cell compartments, it is necessary to determine the molecular weight corresponding to the presence of MAP2 to associate the findings with its isoform to help understand the gene expression observed. The presence of several isoforms for the CP2 and PVDF fibers suggest the protein is being expressed in dendrites and the cells are assuming a neuronal lineage.

Our results have shown the application of a direct current electric field to stimulate PVDF fibers during hMSC culture to be promising. The incorporation of electrical stimuli in a 3D scaffold by employing an electroactive polymer, such as PVDF, provides another level of stimuli during in vitro culture and brings us closer to mimicking in vivo conditions.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. An assembly configured to utilize stimuli through bioactive fibers comprising:
  a first substrate film;
  a first electrode and a second electrode disposed on said first substrate film; and
    a layer that comprises a plurality of aligned, electrospun-piezoelectric polymer fibers, such that the layer of aligned, electrospun piezoelectric polymer fibers forms:
- a first outer periphery region configured to be connected to said first electrode;
- a second outer periphery region configured to be connected to the second electrode; and
- an inner region that is suspended over a bottom surface between the first electrode and second electrode.

2. The assembly of claim 1, wherein the layer is a first layer and the assembly comprises a second layer having a plurality of aligned, electrospun piezoelectric polymer fibers,
such that the second layer forms:
- a first outer periphery region configured to be connected to a third electrode on a second substrate film;
- a second outer periphery region configured to be connected to a fourth electrode on the second substrate film; and
- an inner region that is suspended over a bottom surface located between the third electrode and the fourth electrode; and
the said second substrate film is layered on the first substrate film in a configuration that permits electrical stimulation of the first layer independent of the second layer.

3. The assembly of claim 2, wherein the first layer and the second layer are independently connected to individual voltage sources.

4. The assembly of claim 1, wherein the plurality of aligned, electrospun piezoelectric polymer fibers of the layer comprises polyvinylidene fluoride (PVDF).

5. The assembly of claim 1, further comprising human mesenchymal stem cells and effective cell culture media.

6. The assembly of claim 1, further comprising induced pluripotent stem cells and effective cell culture media.

7. The assembly of claim 1, further comprising embryonic stem cells and effective cell culture media.

8. The assembly of claim 1, wherein the plurality of aligned, electrospun piezoelectric polymer fibers of layer are substantially parallel to one another.

9. The assembly of claim 2, wherein the plurality of aligned, electrospun piezoelectric polymer fibers of the first layer are substantially parallel to one another, and wherein the plurality of aligned, electrospun piezoelectric polymer fibers of the second layer are substantially parallel to one another.

10. The assembly of claim 1, wherein an electrical stimuli is applied to the comprising the plurality of aligned, electrospun piezoelectric polymer fibers.

11. The assembly of claim 1, wherein said first substrate film is a pre-electroded substrate film, and wherein said first and second electrodes are configured to be deposited onto said first substrate film prior to attachment of said layer comprising the aligned, electrospun piezoelectric polymer fibers to said pre-electroded substrate film.

12. The assembly of claim 1, wherein said fibers are connected to said first and second electrodes with a silicon adhesive.

13. The assembly of claim 1, wherein said first and second electrodes are comprised of gold.

14. The assembly of claim 1, wherein said layer is porous.

15. The assembly of claim 14, wherein the second layer is porous.

16. A three dimensional scaffolding system configured to transmit stimuli through fibers comprising:
- a first layer of aligned electrospun piezoelectric polymer fibers provided on a first substrate film;
- a second layer of aligned electrospun piezoelectric polymer fibers provided on a second substrate film; and
- an electrical stimulation system configured to selectively apply electrical stimulation to the first layer of fibers independently of the second layer of fibers, comprising:
- a first electrode and a second electrode disposed on the first substrate film configured to independently apply electrical stimulation to the first layer by enabling the conversion of the applied electrical stimulation to a mechanical strain on the fibers of the first layer on a molecular level without eliciting a mechanical response at a macroscale level; and
- a third electrode and a fourth electrode disposed on the second substrate film configured to independently apply electrical stimulation to the second layer by enabling the conversion of the applied electrical stimulation to a mechanical strain on the fibers of the second layer on a molecular level without eliciting a mechanical response at a macroscale level.

17. The three dimensional scaffolding system of claim 16, wherein the electrical stimulation system is configured to provide electrical stimulation at about 9 mV/cm.

18. The three dimensional scaffolding system of claim 16, wherein the electrical stimulation system is configured to provide electrical stimulation below 10 mV/cm.

19. An assembly configured to utilize stimuli through bioactive fibers comprising:
- a first substrate film;
- a first electrode and a second electrode disposed on said first substrate film; and
- a non-woven layer of aligned, electrospun piezoelectric polymer fibers having:
  - a first outer periphery region configured to be connected to said first electrode;
  - a second outer periphery region configured to be connected to the second electrode; and
  - an inner region that is suspended over a bottom surface between the first electrode and second electrode.

* * * * *